United States Patent

Aznoian et al.

[11] Patent Number: 5,921,915
[45] Date of Patent: Jul. 13, 1999

[54] DIRECTIONAL SURGICAL DEVICE FOR USE WITH ENDOSCOPE, GASTROSCOPE, COLONOSCOPE OR THE LIKE

[75] Inventors: Harold M. Aznoian, N. Andover, Mass.; Ronald B. Lamport, Pelham; Frank Patterson, Exeter, both of N.H.

[73] Assignee: C.R. Bard, Inc., Murray Hill, N.J.

[21] Appl. No.: 08/846,263

[22] Filed: Apr. 30, 1997

[51] Int. Cl.$^6$ ........................................................ A61B 1/04
[52] U.S. Cl. .......................... 600/104; 600/123; 606/205
[58] Field of Search ..................................... 600/104, 123; 606/205, 206, 207, 107, 4; 433/141; 604/902

[56] References Cited

U.S. PATENT DOCUMENTS 4,880,015  11/1989  Nierman .
5,624,379   4/1997  Ganz et al. .

FOREIGN PATENT DOCUMENTS 94 19 137   1/1995  Germany .
WO 97/13463  4/1997  WIPO .

Primary Examiner—Beverly M. Flanagan
Attorney, Agent, or Firm—Darby&Darby

[57] ABSTRACT

A surgical instrument assembly has an endoscope with an instrument channel and a sheathed elongate tubular member inserted into the instrument channel. The sheath is provided with a distal end portion having at least one resiliently biased, curved portion tending to direct the tip of the distal end portion in a direction angularly offset from the axis of the body insertion tube at its distal end. The elongate tubular member is itself longitudinally slidably positioned within the sheath. The instrument channel exerts forces sufficient to straighten the curved portions of the sheath when the curved portions are positioned within the body insertion tube, proximal of the tube's distal end. An elongate flexible endoscopic instrument is mounted into the tubular member so that an operative tip is located at a distal end of the tubular member.

13 Claims, 6 Drawing Sheets

DIRECTIONAL SURGICAL DEVICE FOR USE WITH ENDOSCOPE, GASTROSCOPE, COLONOSCOPE OR THE LIKE

FIELD OF THE INVENTION

The invention relates to the field of surgical instruments and, more specifically, to remotely operable surgical devices used in conjunction with endoscopes, gastroscopes, colonoscopes and similar elongated diagnosis and treatment instruments used to guide such remotely operable surgical devices to surgical sites within a patient's body. The invention also relates to methods for using such remotely operable surgical devices in conjunction with endoscopes, gastroscopes, colonoscopes and the like.

BACKGROUND OF THE INVENTION

In obtaining a biopsy of a patient's esophageal or other tract organ tissues via an end-viewing endoscope, the distal end of the scope must be turned to the side to aim the instrument in the direction of the tissues to be sampled in order to correctly direct a biopsy needle or forceps as such instrument emerges from the distal end opening of the instrument lumen of the endoscope. In addition, the conical field of view provided by the endoscope's optical element is generally on the order of about 90°, centered along the axis of the scope's distal end portion. This procedure is frequently difficult, however, owing to the narrowness of the esophagus. Although a side-viewing endoscope can be used to obtain an esophageal biopsy, the scope is nearly useless in examining the stomach, thus often necessitating use of both an end-viewing endoscope and a side-viewing endoscope during the same surgical procedure. Accordingly, a need exists for a device to facilitate the obtaining of an esophageal or other narrow tract organ biopsy via an end-viewing endoscope.

Some endoscopes include two separate biopsy channels for the simultaneous insertion of multiple endoscopic instruments. In addition, U.S. Pat. Nos. 5,025,778 and 4,646,722 to Silverstein et al. disclose the application, to endoscope insertion members, of removable sheaths having expandable biopsy channels. Such endoscope sheaths enable any existing endoscope to be retrofitted to have multiple biopsy channels. Such multiple biopsy channels, however, cannot be used to their full potential, without the existence of flexible endoscopic instruments with distal end portions which can be turned or directed by an operator at the proximal ends of the instruments. One solution is to provide each endoscopic instrument with its own set of orientation control cables. Although this solution is certainly feasible, a less expensive solution would be beneficial.

Another proposed solution is disclosed in U.S. Pat. No. 5,386,818, which discloses an endoscopic instrument comprising an endoscope insertion tube provided with a biopsy channel and an elongate tubular member inserted into the biopsy channel, the tubular member being provided with a distal end portion having a spring bias tending to form the distal end portion into an arcuate configuration. The tubular member is longitudinally slidable in the biopsy channel, whereby the distal end portion may be alternately maintained in a relatively straightened configuration in a distal end of the biopsy channel and moved outside of the biopsy channel to assume the arcuate configuration. An elongate flexible endoscopic instrument is slidably inserted into the tubular member so that an operative tip at a distal end of the instrument may project outwardly from the distal end portion upon an ejection of at least a part of the distal end portion of the tubular member from the biopsy channel. Such apparatus suffers from a number of disadvantages, however, due to the limited field of vision at the distal end of the scope. Because the spring-biased portion of the tubular member starts to bend as soon as it is extended beyond the tip of the endoscope, the end of the tubular member quickly directs the instrument to a location potentially outside the operator's field of view. Upon further movement of the tubular member distally of the scope's tip, the tubular member turns back on itself, directing the instrument to a position proximal to scope tip and completely out of view of the operator. Thus, while the instrument disclosed in U.S. Pat. No. 5,386,818 may be satisfactory for some procedures, a surgical instrument which remains in the operator's field of view when directed perpendicular to the scope's axis would be particularly advantageous.

SUMMARY OF THE INVENTION

An object of the present invention is to provide a surgical device utilizable with an endoscope, gastroscope, colonoscope or other flexible or rigid elongated diagnostic and/or treatment tool which device is more easily guided to a surgical or diagnostic site within a patient's tract organ or other remote internal body portion.

A related object of the present invention is to provide a method for facilitating the performance of a surgical operation, e.g., the taking of a biopsy, via an endoscope or similar instrument.

Another, more particular, object of the present invention is to provide such a device which is inexpensive to manufacture and easy to use.

A further object of the present invention is to provide a method and/or an associated instrument assembly or apparatus for use in directing the distal end of a surgical instrument distally out of the end of an endoscope and then laterally toward a surgical site in controlled, repeatable fashion, and always within the scope operator's field of view.

Another specific object of the present invention is to provide such a method and/or an associated instrument assembly or apparatus which reduces the costs of endoscopic procedures.

An improved surgical instrument assembly comprises, in accordance with the present invention, an endoscope or other body insertion tube provided with an instrument channel and a sheathed elongate tubular member inserted into the instrument channel. The tubular member is provided with a distal end portion having a pair of resilient curved portions tending to direct the tip of the distal end portion in a direction angularly offset from the axis of the body insertion tube at its distal end. The elongate tubular member is longitudinally slidably positioned within a relatively stiff, straight sheath having mechanical properties sufficient to straighten the curved portions of the tubular member when the curved portions are positioned within the sheath, proximal of the sheath's distal end. An elongate flexible endoscopic instrument is mounted into the tubular member so that an operative tip is located at a distal end of the tubular member. Alternatively, an endoscopic instrument may be slidably housed in the tubular member and may be projectable outwardly from the distal end of the tubular member.

In another embodiment of the invention, the relatively stiff sheath may have resilient curved portions preformed therein, and the tubular member/endoscopic instrument assembly may be straight in its unstressed or relaxed condition. The curved portions of the sheath, in this case, would only assume their curved configurations in the absence of a straightening force applied thereto by the endoscope's instrument channel walls.

A method of performing endoscopic, gastroscopic, colonoscopic or similar procedures comprises, in accordance with the present invention, the steps of (a) providing an endoscope or the like having an instrument channel, (b) providing a sheathed elongate tubular member insertable into the biopsy channel, the tubular member being formed with a distal end portion having a pair of resiliently curved portions tending to direct the tip of the distal end portion in a direction angularly offset from the axis of the body insertion tube at its distal end, (c) providing an elongate flexible endoscopic instrument mounted in or slidably insertable into the tubular member, the instrument having an operative tip at a distal end, (d) inserting a distal end segment of the insertion tube into a patient, (e) pushing the sheathed tubular member in a distal direction to eject at least a part of the sheathed distal end portion thereof from the instrument channel, in the patient, and (f) while maintaining the distal end of the sheathed tubular member within the operator's field of view, advancing the tubular member with respect to the sheath, thereby selectively causing one or both curved portions of the tubular member to be ejected distally from the sheath and thereby causing the end of the tubular member to deflect a predetermined angle with respect to the longitudinal axis of the scope under the action of the tubular member's resilient bias force. Subsequent steps include (g) operating on internal tissues of the patient with the operative tip.

According to more specific features of the present invention, the method further comprises the step of disposing a portion of the sheathed tubular member within the instrument channel prior to the introduction of the endoscope or similar body insertion tube into the patient. This step is particularly useful where the instrument channel is a permanent part of the endoscope or body insertion tube. In addition, the endoscopic instrument may be inserted into the tubular member prior to the disposition of the sheathed tubular member inside the instrument channel of the body insertion tube.

Alternatively, the endoscopic instrument or the like may be inserted into the sheathed tubular member only upon at least partial disposition of the tubular member inside the instrument channel of the scope or other device.

Where the endoscope or body insertion tube is flexible and provided with actuator means for controlling a distal end orientation thereof, the method further comprises the step of operating the actuator means to turn the distal end of the body insertion tube upon at least partial insertion of the body insertion tube into the patient, positioning the distal end portion of the tubular member within the turned portion of the body insertion tube, and advancing the tubular member with respect to the sheath, thereby causing the tubular member to become oriented in a predetermined direction as a result of the tendency of the curved portions thereof to follow the turn of the distal end of the body insertion tube.

The extent to which the tubular member projects from the relatively stiff sheath will determine the angle between the distal end portion of the tubular member and the axis of the endoscope or body insertion tube at the distal end thereof, i.e., whether one or both curved portions are advanced beyond the distal tip of the sheath. Thus, to control the angular orientation of the instrument with respect to the axis of the endoscope once the distal end of the sheath is projecting distally of the endoscope's distal end, the operator controls the relative axial positions of the tubular member and the sheath, independent of how far beyond the distal end of the instrument channel the sheath is advanced.

Other embodiments of the invention may include an elongate tubular member having more than two curved portions, i.e., three or more such curved portions. In this manner of construction, the oblique angle of approach is more finely controllable, according to the number of curved portions ejected distally from the sheath.

A device and method in accordance with the present invention greatly facilitates the performance of endoscopic, gastroscopic, colonoscopic and other similar tract organ or remote surgery by facilitating the guiding of a surgical instrument to a surgical site.

BRIEF DESCRIPTION OF THE DRAWINGS

These and other objects of the present invention will be apparent from the drawings and detailed descriptions herein, in which.

DETAILED DESCRIPTION OF THE INVENTION

Figure 1:
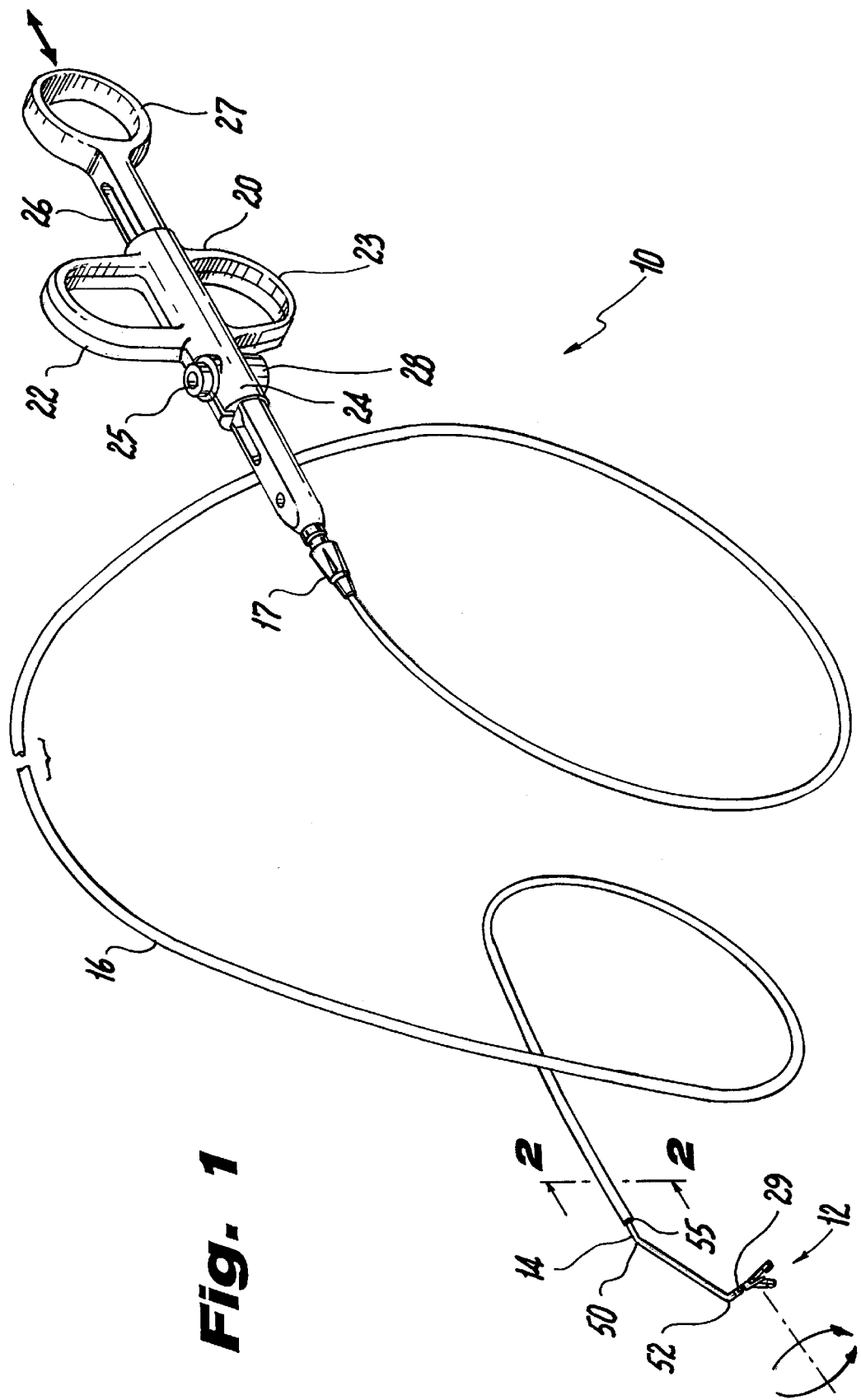
FIG. 1 is a schematic side perspective view of an embodiment of the invention.

A directional surgical device 10 is seen in FIG. 1 as having particular use in connection with an endoscope, gastroscope, colonoscope or other elongated flexible surgical appliance. In the illustrated embodiment of the invention, the device 10 is a biopsy forceps tool, although any small endoscopic or similar type of instrument may find advantageous utility according to this invention. The directional surgical device 10 includes remotely actuatable forceps jaws 12 hingedly mounted at the distal end of a sheathed elongate tubular member 14. The tubular member 14 is connected at its proximal end to an instrument control handle 20. The control handle 20 is conventional in all respects and is commercially available from numerous suppliers.

Slidably mounted on the tubular member 14 is a relatively stiff sheath 16 having a length which is slightly shorter than the length of the tubular member 14, the purpose of which will be further explained below. The overall length of the device 10 will vary according to the particular surgical tool and the particular body insertion tube for which it is intended. In the presently described embodiment, the overall length is about 180 centimeters.

A fitting 17 is attached to the proximal end of the sheath 16 for providing a gripping or holding point by which to manipulate the relative axial position of the sheath 16 with respect to the tubular member 14. The fitting 17 is preferably removably but firmly connectable to the control handle 20, such as by frictional engagement of mating parts, by mating Luer-type connector parts, or by any other known mechanism.

The control handle 20 includes finger rings 22,23 integrally molded with a generally cylindrical housing 24 and an axially slidable control shaft 26 passing through the housing 24 for operation of the forceps jaws 12, the shaft 26 having a thumb ring 27 at its proximal end. The proximal end of the tubular member 14 is fixedly connected to the distal portion of the control shaft 26. In conventional fashion, a pull or control wire 30 (see FIG. 2) passes through a central lumen 32 within the tubular member 14, and is connected at its distal end to the proximal ends of the forceps jaws 12, and at its proximal end to a screw clamp 28 or other securing mechanism which is integrally formed with or otherwise part of the housing 24 of the control handle 20. The forceps jaws 12 are, in turn, hingedly connected to a forceps jaw mounting body 29 which is rigidly connected to the end of the tubular member 14.

By the just-described construction, which is illustrative only, and in a manner extremely well known to those of ordinary skill in the art, relative axial movement of the pull wire with respect to the tubular member 14, by moving the thumb ring 27 proximally and distally with respect to the finger rings 22,23, respectively, causes the forceps jaws 12 to open and close. It will be readily understood by those of ordinary skill in the art that numerous other instrument actuation mechanisms may be employed in other embodiments of the invention. The invention does not reside in the use of any particular instrument or actuation method, but instead concerns the nature, construction and use of the tubular member 14 and the longitudinally slidable sheath 16 thereover, as will be explained in greater detail below.

Moreover, the control handle 20 may include an electrical connector 25 or other conductive attachment device for providing surgically useful electrical energy, such as low or high voltage direct current or alternating current, or radio-frequency (rf) or microwave energy, or any other therapeutic energy, from an external source of such energy to the particular surgical instrument mounted on the distal end of the tubular member 14. Other such surgical instruments might not include any moving parts, and therefore would not require the particular type of actuating handle described above in connection with the presently described embodiment.

In still other cases, the surgical instrument might not even be mounted on the tubular member 14, and may simply be insertable into the tubular member 14 after the distal end portion of the tubular member 14 has been appropriately positioned by the device operator. According to the requirements of still other embodiments, one or more fluid flow paths, with associated fluid flow controls, may be provided in a suitable control handle in accordance with the invention. Some examples of surgical instruments which may be constructed according to the principles of the invention are sclerotherapy needles, hemostasis probes, electrosurgical needles and other electrodes, infusion or aspiration or biopsy needles, graspers, scissors or other cutters, cauterization snares or probes, laser fiber optics, etc., without limitation.

The tubular portion 14 may be rotatable about its own longitudinal axis, as shown by the arrows in FIG. 1.

Figure 6:
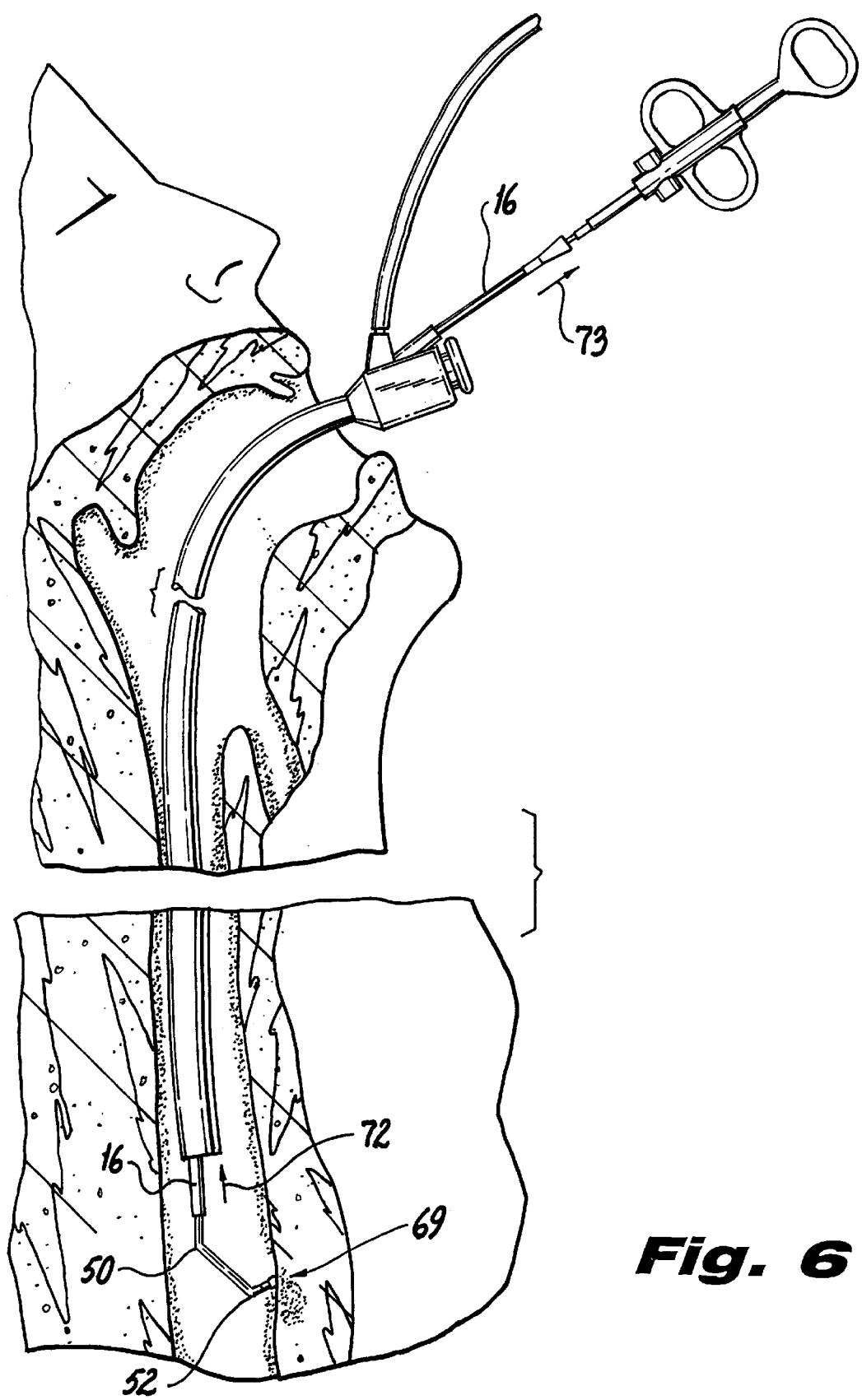
FIGS. 6–7 are partial sectional views of the embodiment of FIG. 1 at different steps of a surgical procedure performed according to the invention.

As illustrated in FIG. 6, the sheathed tubular member 14 is insertable through an instrument channel of an endoscope or other body insertion tube 40 which is conventionally also provided with a fiber-optic illumination source, a fiber-optic image system including a viewing lens at the insertion tube's distal end, and some steering mechanism such as tensioning cables for controlling the orientation of the distal end of the insertion tube 40. All of the mechanical and functional details of the insertion tube 40 are entirely conventional in this described embodiment of the invention.

Figure 2:
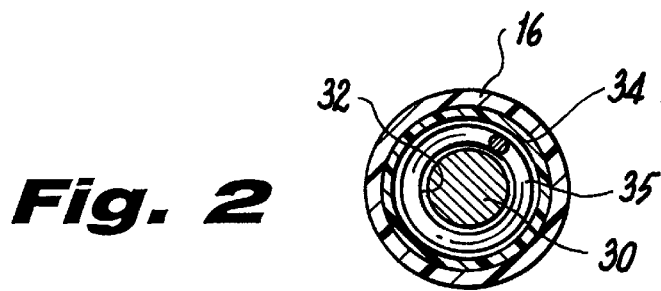
FIG. 2 is a cross sectional view of the device of FIG. 1 taken along line 2—2.
Figure 3:
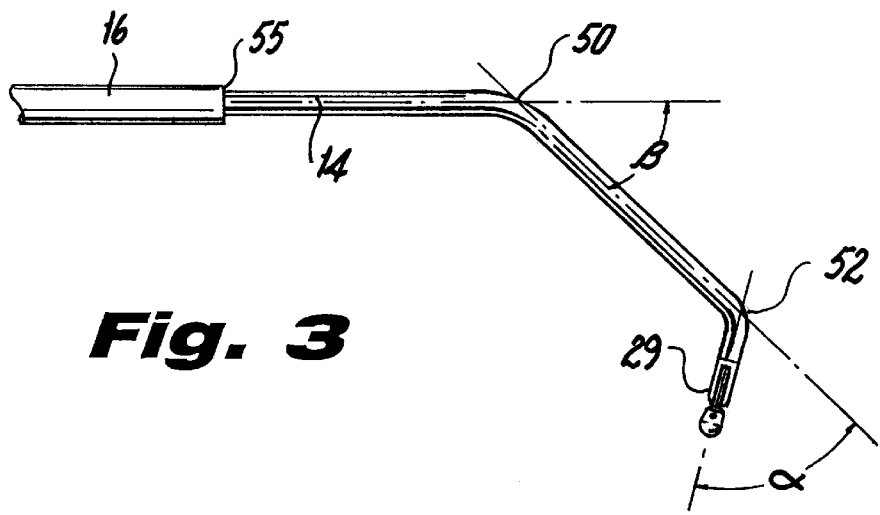
FIG. 3 is a partial schematic side perspective view of the embodiment of FIG. 1.

As seen in cross section in FIG. 2, the outer, relatively stiff sheath 16 closely houses the elongate tubular member 14 which, in the presently described embodiment, is a polytetrafluoroethylene (PTFE) jacketed (jacket: ref. no. 34) 0.016 inch diameter 302/304 stainless steel spring temper wire coil 35. Torque transmitting capability may be provided to the wire coil by, for example, joining (e.g., by spot-welding) adjacent coils at given coil intervals, such as every third coil or the like. Alternatively, other tubular constructions may be employed, such as braided tube constructions, which have good torque transmission characteristics.

The control wire 30 is also stainless steel in this embodiment of the invention.

The sheath 16 preferably comprises an extruded tube made of polyetheretherketone (PEEK) resin having an inside diameter of about 0.081 inch and tubing wall thickness of about 0.005 inch. A preferred PEEK material is VICTREX 450P, available from ICI Americas, Inc., of Wilmington, Del. Other suitable materials for the sheath 16 include TECOPLAST® Op-570-341 resin available from Thermedics, Inc., of Woburn, Mass., and PEBAX® polyether block amide thermoplastic elastomers suitable for extrusion molding applications, available from Atochem North America, Plastics Additives Division, of Cleveland, Ohio. The sheath 16 and the PTFE-jacketed coil 35 forming the tubular member 14 have such surface lubricity characteristics that the tubular member 14 relatively easily slides proximally and distally within the sheath 16, which relative ease of sliding motion is an important feature of the invention.

Referring to FIGS. 1 and 3–5, the tubular member 14 is shown as being provided with a first, proximal bend 50 and a second, distal bend 52 in the same angular direction and plane as the proximal bend 50. It is expected by the inventors that the optimum angles and positions of these bends 50,52 relative to the surgical tool will vary according to the different uses of particular surgical instruments. However, a presently preferred embodiment includes a distal bend 52 located approximately one centimeter proximal of the surgical instrument's tip, with the proximal bend 50 located about four centimeters proximal of the distal bend 52. The distal bend angle $\alpha$ is preferably in the range of about 25° to 60°, and the proximal bend angle $\beta$ is preferably in the range of about 15° to 45°. The tubular member 14 assumes the doubly bent shape illustrated in FIG. 3 only when both the distal bend 52 and proximal bend 50 have been ejected from the distal end 55 of the sheath 16.

Figure 4:
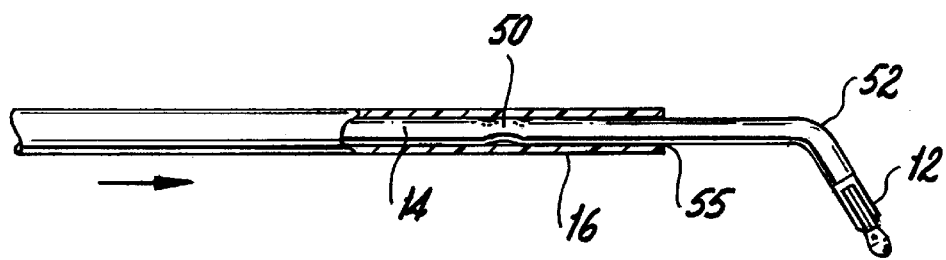
FIGS. 4–5 are partial sectional views of the embodiment of FIG. 1 at different steps of operation of the apparatus according to the invention.

In the relative axial positions of the components shown in FIG. 4, the distal bend 52 is present but the proximal bend 50 is not, the tubular member 14 having been straightened by distal advancement (in the direction of the arrow) of the relatively stiff sheath 16. In many particular applications, the operator will elect to extend only the distal bend 52 beyond the distal end of the endoscope, while maintaining the proximal bend 50 within a curved end portion of the scope, either inside or out of the sheath 16, as will be explained further below.

Figure 5:

By continued distal advancement of the sheath 16 over the tubular member 14, both the proximal bend 50 and the distal bend 52 are straightened within the sheath 16 (see FIG. 5). The physical characteristic of the sheath 16 that it is sufficiently flexible to pass inside the curved instrument channel of an endoscope, yet sufficiently stiff to straighten the bends placed in the tubular member 14, is an important feature of the present invention.

It will be understood that other embodiments of the invention can include elongate tubular members having more than, or less than, two bends in their distal end portions. For example, certain surgical tools may be most advantageously positioned at a known, specific angle. For applications requiring the greatest degree of angular accuracy, a single bend may be preferable to two or more bends. For certain other applications, a plurality of separate bends may be useful in permitting the operator to select the particular oblique angle of approach within a wider range of options, depending upon the number of curves ejected from the distal end of the sheath.

Figure 9:
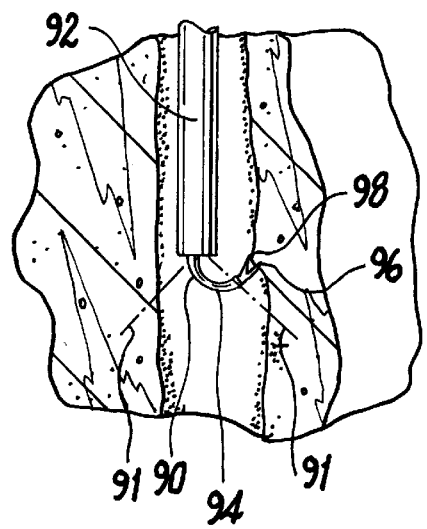
FIG. 9 is a partial schematic sectional view of a prior art surgical device.

Now turning to FIG. 9, there is shown a prior art device aimed at solving many of the same problems addressed by the present invention, which device is described in detail in U.S. Pat. No. 5,386,818. That device comprises a tubular member 90 having a distal end portion 94 provided with a spring bias or memory tending to form the distal end portion into an arcuate configuration, e.g., a substantially U-shaped configuration. The degree of bending of the distal end portion 94 of the tubular member 90 is determined by controlling the degree of ejection of the distal end portion 94 from the biopsy channel of an endoscope 92. The more tubular member 90 is pushed in the distal direction, the greater the angle that a tip 96 of the tubular member 90 bears with respect to a longitudinal axis of the biopsy channel. Upon the attainment of a desired angle of approach, an elongate flexible endoscopic instrument is slidably inserted through the tubular member 90 so that an operative tip 98 at a distal end of the instrument projects outwardly from distal end portion 94. Thus, tubular member 90 serves as an instrument guide for controlling the orientation of the operative tip 98 with respect to the endoscopic insertion tube 92.

As further seen in FIG. 9, the prior art device suffers several disadvantages in use. As shown in dashed lines 91, the endoscope operator's distal field of vision is typically on the order of 90°, centered along the scope's longitudinal axis. Upon pushing the pre-curved tubular guide member 90 distal of the end of the endoscope's biopsy channel, the tubular member tip 96 quickly passes out of the operator's field of view. Merely advancing the tubular member 90 further distally does not solve this problem, for while the tubular member tip 96 may thus come back into view, it is only positionable in its fully U-shaped configuration, and cannot conveniently be used to deliver the instrument operative tip 98 to the wall of the tract organ at an oblique angle. Furthermore, since the curving action of the distal end portion 94 occurs as soon as the portion 94 begins to emerge from the biopsy channel, this feature of the prior art device may only be useful at surgical sites permitting access by the full outside diameter of the endoscope.

Figure 7:
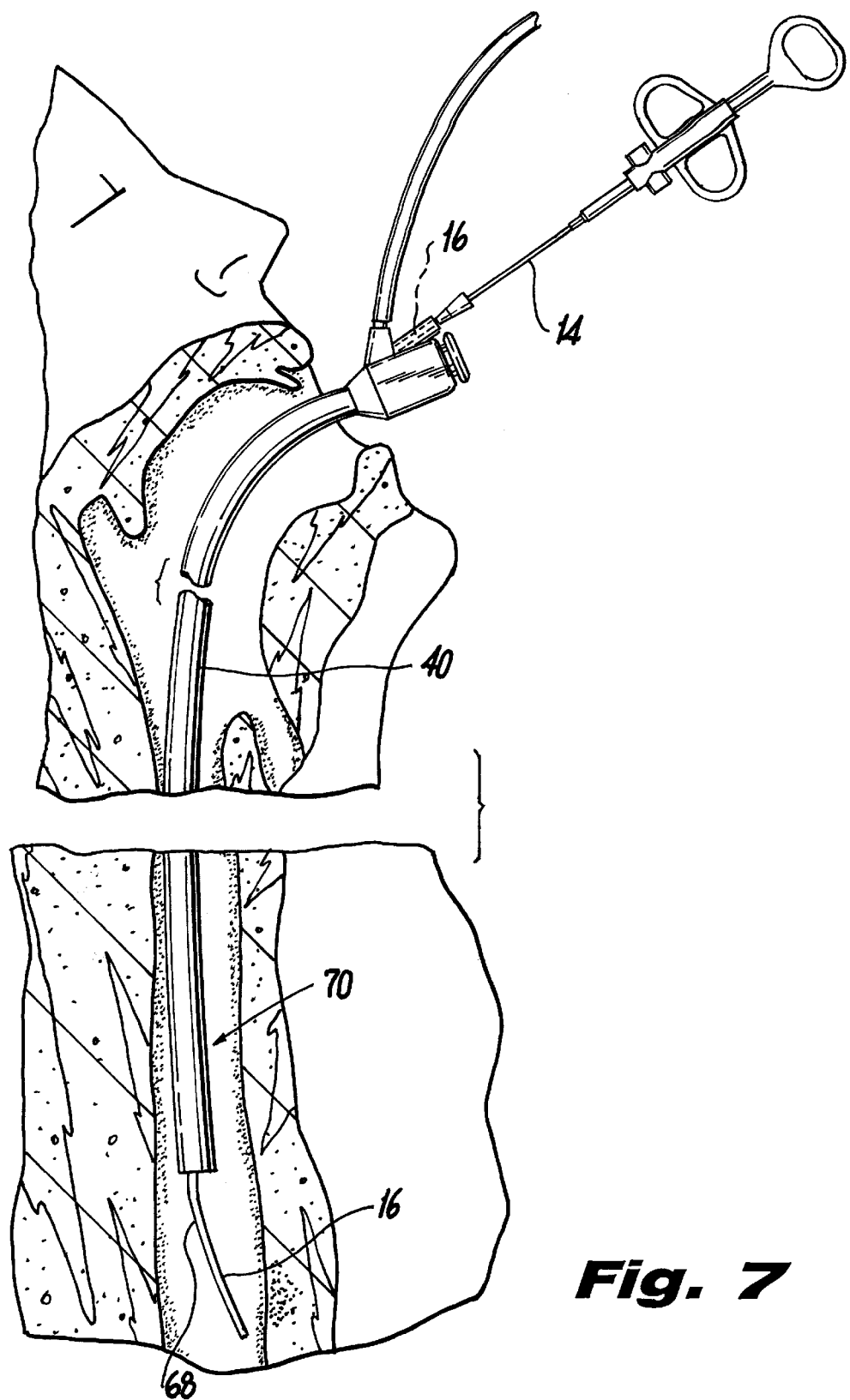
Figure 10:
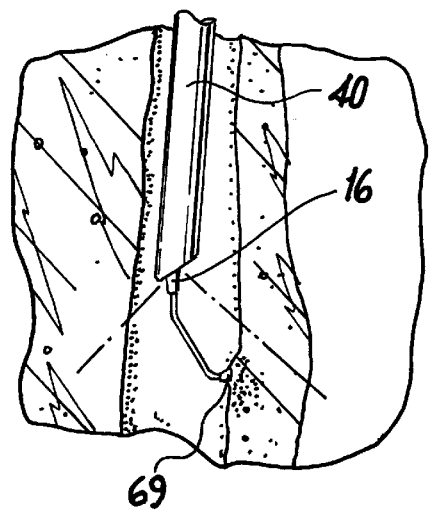
FIG. 10 is a partial schematic sectional view of an embodiment of the invention in use.

In contrast, referring to FIGS. 6, 7 and 10, the improved surgical instrument assembly of the present invention allows an oblique angle approach to tract organ surgical sites which are too small to be conveniently accessible by the full outside diameter of the endoscope, and with the surgical instrument tip always maintained in the operator's field of view. FIGS. 6 and 7 illustrate particular steps in the diagnostic or treatment procedure, as now explained. An endoscope or body insertion tube 40 having a longitudinal instrument channel therethrough has been provided. A sheathed elongate tubular member 14 has been inserted into the biopsy or instrument channel, with the sheath 16 advanced distally so that the sheath 16 fully houses the entire distal end portion 68 of the tubular member 14, including an operative tip 69 mounted on the distal end of the tubular member (see FIG. 6). A distal end segment of the endoscope 40 has been inserted into a patient's esophagus 70. The sheathed tubular member 14 has been pushed in a distal direction to eject at least a part of the sheathed distal end portion 68 thereof from the instrument channel, in the patient. Finally, as shown in FIG. 7, while maintaining the distal end of the sheathed tubular member 14 within the operator's field of view, the tubular member 14 has been advanced distally with respect to the sheath 16 (by moving the sheath 16 proximally as shown by the arrows 72,73), thereby selectively causing both curved portions 50,52 of the tubular member 14 to be ejected distally from the sheath 16 and thereby causing the end of the tubular member 14 to deflect a predetermined angle with respect to the longitudinal axis of the scope under the action of the tubular member's resilient bias force. Subsequent steps (not shown) include operating on internal tissues of the patient with the operative tip 69.

Numerous variations of this procedure are possible, all being well within the scope of the invention. Depending upon the nature of the surgical procedure, the particular body insertion tube and the surgical instrument involved, the order of steps by which the final operative position is achieved will vary greatly. For example, the sheathed tubular member may be inserted into an already-positioned endoscope. In some cases where the surgical instrument is removably insertable into the tubular member, the sequential time or step at which the instrument is inserted into the tubular member will be a matter of operator's choice. The variations are as numerous as there are different preferences for performing different procedures using, e.g., endoscopes, bronchoscopes, colonoscopes, gastroscopes, uteroscopes, laparoscopes and the like.

As shown in FIG. 10, the operative tip 69 remains well within the operator's field of view, both when inside the sheath 16 and when in its angled configuration for approaching the surgical site. With a suitably long device, the sheathed tubular member 14 may be extended a considerable distance distally beyond the end of the body insertion tube 40, before withdrawing the sheath 16 to angle the operative tip 69. Since the outside diameter of the sheath 16 is so much less (a preferred device according to the invention fits within a 5 French instrument channel) than that of the body insertion tube or endoscope 40, the operator may deliver the operative tip 69 to surgical sites which might be otherwise inaccessible to the endoscope, or to the prior art device described and illustrated in U.S. Pat. No. 5,386,818.

Figure 8:
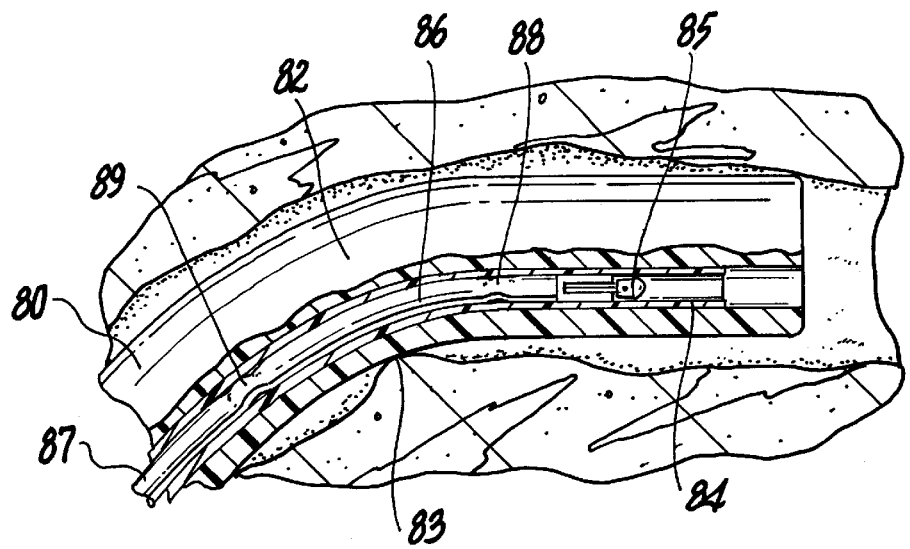
FIG. 8 is a partial schematic sectional view of an embodiment of the invention at a step of a surgical procedure according to the invention.

A further feature of the invention is the ability, provided to the endoscope operator, to position the plane of the proximal bend 50 and distal bend 52 in a desired angular position about the longitudinal axis of a steerable or deflectable endoscope or similar device having a controllable, deflectable end portion. In such an endoscope 80 as is illustrated in FIG. 8, the distal end portion 82 thereof may be steered or deflected to navigate a corner 83 or bend in the patient's internal anatomy, as is conventionally done. Upon achieving the illustrated configuration of the scope 80, the operator may then withdraw proximally the sheath 84 from the distal end portion 86 of the tubular member 87 so as to unsheath the distal bend 88 and the proximal bend 89 therein. The bias forces in the tubular member 87 as a result of the bends 88,89 therein, coupled with the lubricious characteristics of the PTFE jacket, permit the device to rotate on its own axis toward the most relaxed angular orientation, in which the plane of the bends 88,89 coincides with the plane of the curved endoscope distal end portion 82, which planar orientation is known to the operator. The operative tip 85 may then be advanced distally and ejected out of the instrument channel, or else, once properly angularly oriented, the tubular member distal end portion 86 may be resheathed and advanced to a surgical site in the operator's field of view in the sheathed condition. In a situation where the surgical site is close to the endoscope's distal end, the operator may simply extend the distal end portion 86 only so far as to eject the distal bend 88 from the instrument channel, while maintaining the proximal bend 89 within the curved end portion of the endoscope. Such use also provides rotational angular control and predictability of operative tip direction for the operator. In this way, additional control over the position of the distal end of the surgical device of the present invention is achieved.

Figure 11:
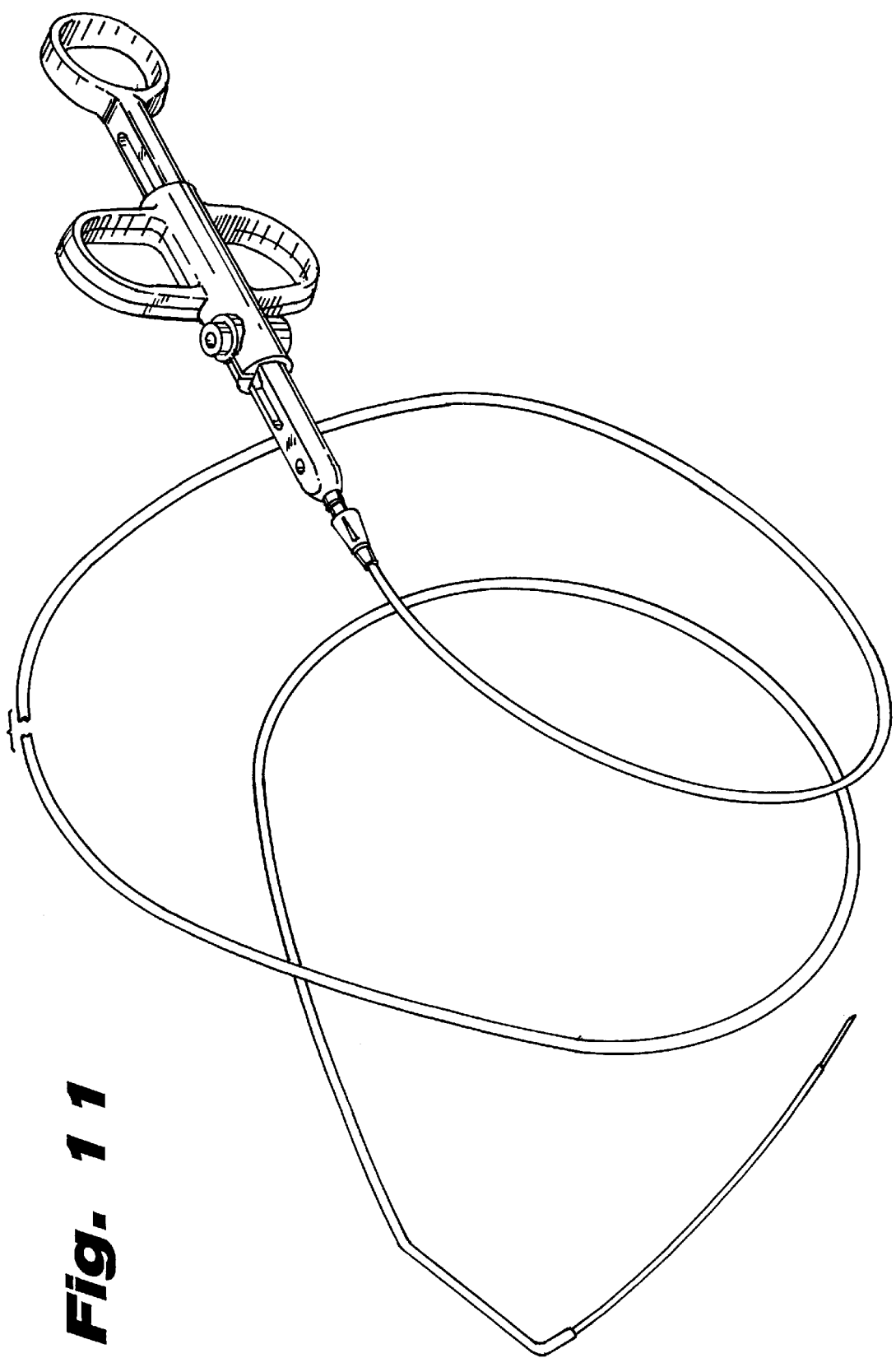
FIG. 11 is a partial schematic view of an alternative embodiment of the invention.

Referring, finally, to FIG. 11, an alternative embodiment of the invention is illustrated and now described. In this embodiment, which may be particularly advantageous for certain surgical procedures, at least one angular bend is formed in a distal end portion of the sheath itself, while the flexible tubular member carrying or delivering the operative tip or other surgical instrument to the surgical site is generally straight, in the absence of any external forces. The presently preferred version of this embodiment includes two bends. The sheath is maintained in a generally straightened condition while inside the instrument channel of the endoscope or similar body insertion tube, by the straightening forces applied thereto by the walls of the instrument channel. Upon further distal advancement of the sheath in the scope's instrument channel and beyond the distal end of the endoscope, the sheath will selectively assume either its singly bent or doubly bent configuration depending upon how far out of the instrument channel the sheath is advanced. Upon the operator's positioning of the distal end of the sheath in the desired position and at the desired oblique angle of approach to the surgical site, the slidably housed tubular member may be advanced distally with respect to the sheath in order to advance the operative tip thereon or therein to the site.

As was the case for the previously described embodiments, the sheath of FIG. 11 may be positioned so that the proximal bend is positioned within a curved end portion of the endoscope or similar body insertion tube, with the effect that the proximal bend will tend to follow the curve of the scope's distal end portion. In this manner, the distal bend of the sheath will be predictably oriented in a direction which is controllable by the operator.

It is to be understood that the drawings and descriptions herein are proferred by way of example to facilitate comprehension of the invention and should not be construed to limit the scope thereof.

While the invention has been particularly shown and described with reference to the preferred embodiments thereof, it will be understood by those skilled in the art that various changes in form and detail may be made therein without departing from the spirit and scope of the invention.

What is claimed is:

1. A surgical assembly comprising:

an elongate body insertion tube having a longitudinally extending instrument channel therethrough;

an elongate, flexible yet relatively stiff sheath inserted into the channel, the sheath being provided with a distal end portion having a bias tending to form the distal end portion into at least a first, proximal bend in the absence of an external straightening force on the distal end portion, whereby the distal end portion may be alternately maintained in a relatively straightened configuration in a distal end of the body insertion tube and moved outside of the body insertion tube to selectively assume at least a singly bent configuration;

an elongate tubular member inserted into the sheath, the tubular member being longitudinally slidable in the sheath; and an elongate surgical instrument having an operative tip, the instrument being positioned in the tubular member so that the operative tip extends distally from a distal end portion of the tubular member.

2. The assembly defined in claim 1, wherein the sheath comprises a distal end portion having a bias also tending to form the distal end portion into at least a second, distal bend in the absence of an external straightening force on the distal end portion, whereby the distal end portion may be alternately maintained in a relatively straightened configuration in a distal end of the body insertion tube and moved outside of the body insertion tube to selectively assume at least a singly bent or a doubly bent configuration.

3. The assembly defined in claim 1, wherein the tubular member comprises a wire coil having a lubricious surface.

4. The assembly defined in claim 1, wherein the sheath comprises a tube made of polyetheretherketone resin.

5. The assembly defined in claim 1, wherein the body insertion tube includes an image transmission guide for transmitting an image from a distal end of the insertion tube to a proximal end thereof.

6. The assembly defined in claim 2, wherein the first, proximal bend has an angle $\beta$ in the range of about 15° to 45°, and the second, distal bend has an angle $\alpha$ in the range of about 25° to 60°.

7. A device for use in medical procedures involving the use of an elongate body insertion tube having a longitudinally extending instrument channel therethrough, comprising:

an elongate, flexible yet relatively stiff sheath sized so as to be insertable into the channel, the sheath being provided with a distal end portion having a bias tending to form the distal end portion into at least a first, proximal bend in the absence of an external straightening force on the distal end portion, whereby the distal end portion may be alternately maintained in a relatively straightened configuration in a distal end of the body insertion tube and moved outside of the body insertion tube to selectively assume at least a singly bent configuration;

an elongate tubular member inserted into the sheath, the tubular member being longitudinally slidable in the sheath; and an elongate surgical instrument having an operative tip, the instrument being positioned in the tubular member so that the operative tip extends distally from a distal end portion of the tubular member.

8. The device defined in claim 7, wherein the sheth comprises a distal end portion having a bias also tending to form the distal end portion into at least a second, distal bend in the absence of an external straightening force on the distal end portion, whereby the distal end portion may be alternately maintained in a relatively straightened configuration in a distal end of the body insertion tube and moved outside of the body insertion tube to selectively assume at least a singly bent or a doubly bent configuration.

9. The device defined in claim 7, wherein the tubular member comprises a wire coil having a lubricious surface.

10. The device defined in claim 7, wherein the sheath comprises a tube made of polyetheretherketone resin.

11. The device defined in claim 8, wherein the first, proximal bend has an angle β in the range of about 15° to 45°, and the second, distal bend has an angle α in the range of about 25° to 60°.

12. A method for use in surgical procedures, comprising the following steps in the following or any other order:

providing a body insertion tube having a longitudinal instrument channel therethrough;

inserting a sheathed elongate tubular member into said channel, said sheath being formed with a distal end portion having a bias tending to form said distal end portion into at least a first, proximal bend in the absence of an external straightening force on said distal end portion;

placing a distal end portion of the tubular member within the sheath;

providing an elongate flexible surgical instrument in said tubular member, said instrument having a distal operative tip;

inserting a distal end segment of said body insertion tube into a patient;

upon insertion of said distal end segment into a patient, pushing said sheathed tubular member in a distal direction to eject at least a part of said sheathed tubular member from said channel, thereby selectively causing said distal end portion of the sheath to assume at least a singly bent configuration by action of said bias; and moving the tubular member distally with respect to the sheath to eject at least said operative tip from a distal end of the sheath.

13. The method as defined in claim 12, the sheath being further formed with a distal end portion having a bias tending to also form said distal end portion into at least a second, distal bend in the absence of an external straightening force on said distal end portion, further comprising the step of moving the sheath distally in the body insertion tube, and thereby selectively causing said distal end portion to assume at least a singly bent or a doubly bent configuration by action of said bias.

* * * * *